United States Patent [19]

Honstein et al.

[11] Patent Number: 5,098,290
[45] Date of Patent: Mar. 24, 1992

[54] DENTAL MODELING METHOD AND APPARATUS USING APERTURED MATRIX PLATE

[75] Inventors: Jerry P. Honstein, 6543 E. Circulo. Dali, Anaheim Hills, Calif. 92807; Anthony B. Siragusa, Anaheim Hills, Calif.; Richard Barnes, Mission Viejo, Calif.; Victor M. Barajas, San Gabriel, Calif.

[73] Assignee: Jerry P. Honstein, Anaheim Hills, Calif.

[21] Appl. No.: 579,300

[22] Filed: Sep. 7, 1990

[51] Int. Cl.⁵ .............................................. A61C 19/00
[52] U.S. Cl. ........................................ 433/74; 433/49; 433/50
[58] Field of Search ..................... 433/49, 50, 53, 74, 433/72; 264/16, 17

[56] References Cited

U.S. PATENT DOCUMENTS

4,371,339  2/1983  Zeiser ..................................... 433/53
4,708,835  11/1987  Kiefer ..................................... 433/74

*Primary Examiner*—Cary E. O'Connor
*Attorney, Agent, or Firm*—William L. Chapin

[57] ABSTRACT

An improved method and apparatus for making cast dental models having integral dowel pins permitting segments or dies of a model to be attached and re-attached to a base plate in a precise location, by means of holes in the base plate adapted to insertably receive the dowel pins, is disclosed. The apparatus includes a base plate having a generally semi-circular shape, the arcuate outer wall surface of which is modified to have flat walls approximating the shape of a circumscribed polygon. A matrix positioning plate has a polygonal aperture through its thickness dimension adapted to insertably receive the base plate. A negative dental impression is attached to a first, lower surface of the matrix plate, and a transparent transfer plate of the same size and shape as the base plate inserted into the aperture of the matrix plate. Marks are placed at those locations of the transfer plate where dowel pins are desired to engage parts of the dental impression viewed through the transfer plate. The marked transfer plate is then clamped in overlying conformal relationship to a base plate, and holes formed in the base plate at the locations indicated by the marks. In another embodiment of the invention which dispenses with the requirement for a transfer plate, a transparent base plate is inserted into the matrix plate, marked and removed. Holes are then formed in the base plate at the marked locations.

9 Claims, 8 Drawing Sheets

DENTAL MODELING METHOD AND APPARATUS USING APERTURED MATRIX PLATE

BACKGROUND OF THE INVENTION

A. Field of the Invention

The present invention relates to methods and apparatus for making dental models. More particularly, the invention relates to an improved method and apparatus for producing crowns, bridges, tooth prostheses and other dental restorations.

B. Background of the Invention

Dental models are widely utilized in the fabrication of replacements, or restorations, for missing or damaged teeth. Such models are usually produced in a sequence of well-known steps. First, a negative impression is made by a dentist of the upper or lower jaw of a patient, using a flexible, quick-setting resilient molding material, such as liquid latex rubber poured into a holding device. After the rubber has set, the negative impression and holding device are removed from the patient's mouth and positioned so that the openings of the negative impression face upwards. Thus, an upper jaw impression is removed from the mouth retained in the same orientation, while a lower jaw impression is inverted after removing it from the patient's mouth. A jaw impression in a holder is then filled with a liquid plaster material, which is frequently referred to as die stone. After the die stone has hardened, the casting is removed from the flexible dental impression mold.

The casting, or model as it is usually referred to, is a positive replication of that portion of the jaw initially used to make the negative impression mold. Thus, the model is an accurate replica of the teeth and soft tissue of the upper or lower jaw, or a portion thereof, from which a negative impression has been made.

Dental models made as described above usually have an arched shape and are therefore, frequently referred to as dental arches. Such dental arches are usually fastened to some sort of base plate for convenience in performing further steps described below.

The existing art utilizes several techniques of providing a base plate for dental arches. The techniques fall generally into either of two broad method classifications. One method utilizes a base of the gypsum-like die stone that is used to make the arch, and is formed from liquid die stone, after the dental arch is formed, by pouring the liquid die stone into a box form positioned around the outer perimeter of the already hardened dental arch.

The other method of providing a base for a dental arch consists of attaching the arch to a pre-manufactured plate made of dimensionally stable material and having a generally semi-circular shape, the convex surface of which conforms generally to the convex surface of the dental arch.

Bases are provided for dental arches so that the arch may be segmented into individual sections or dies, by means of saw cuts, and removably returned to the original positions of the sections in the arch. Individual sections, or dies, are utilized in the fabrication of dental restorations including dentures, partial dentures, crowns, jackets, bridges, and implant supported restorations. The dies are used as models for making individual restorations of various materials such as gold and other metals, plastics and various ceramic materials. After a restoration has been fabricated, it must be remounted on the arch support base at the precise position that it was removed from, to verify that the restoration is of the precise shape and size to fit properly in the mouth of the patient.

The method of removably attaching individual dies to the arch support base usually consists of molding two dowel pins into each die position of the dental arch, the dowel pins protruding downwards into corresponding holes in the base. Two dowel pins are used to preclude rotation of a die with respect to the base.

Several methods exist for locating dowel pins in desired positions, typically two per tooth, in each die. The accuracy of placement of pins in each die is critical, since even a small placement error could result in the wall of a die breaking through if a saw cut is too close to a pin. Therefore, the preferred method of molding pins into a dental arch and fitting the pins into a base employs a pre-manufactured, pre-fabricated base made of plastic material having greater dimensional stability than the die stone from which the arch is fabricated.

Several systems exist for pouring a dental model utilizing a pre-fabricated, as opposed to a poured, integral base.

One such system, disclosed in Zeiser, U.S. Pat. No. 4,371,339, Denture Mold And Method Of And Arrangement For Its Manufacture, requires the use of a relatively complicated, heavy and expensive orienting apparatus, manufactured to precise tolerances, for holding a dental impression while determining the locations on a pre-fabricated base plate where holes are subsequently to be made for securing dowel pins which will be molded into a dental arch.

Another method and apparatus for making dental models using pre-fabricated base plates is disclosed in Kiefer, U.S. Pat. No. 4,708,835, Nov. 24, 1987, Method And Apparatus For Making A Dental Model Mounted On A Base Plate. In Kiefer, a pre-fabricated base plate containing a plurality of pre-formed holes is fitted with dowel pins in each location where it is desired to make a die removable from the cast dental arch. Two methods of determining which of the pre-formed holes in a base plate are to have dowel pins inserted in them are disclosed. Both methods require that a dental impression be attached to a carrier plate having guide means for removably receiving a base plate in a precisely repeatable orientation with respect to the dental impression. The carrier plate includes a flat base and a vertical wall or upright which protrudes upwards from the rear edge of the base.

One version of the Kiefer method requires the use of a transparent datum plate which is positioned over the base plate and fitted with marker pins at desired locations. The datum plate is then removed from the carrier plate, flipped over and re-mounted on the opposite side of the upright of the carrier plate. A base plate is then mounted to the upright of the carrier plate, over the datum plate, and dowel pins inserted into pre-formed holes in the base plate at those positions occupied by marker pins in the underlying datum plate. Both datum plate, and base plate with dowel pins inserted are then removed from the carrier plate, and the base plate flipped over and remounted to the opposite side of the carrier plate upright, over a dental impression containing freshly poured liquid die stone, and pushed downwards so that the base plate contacts the impression. The dowel pins thus protrude into the liquid die stone, and are thereby secured in the cast dental arch when the die stone hardens.

In a second version disclosed in Kiefer, a transparent base plate having pre-formed blind holes on one side, and depressions on the opposite side of the plate aligned with the holes, for receiving colored marking ink, is placed over a dental impression. Those depressions are locations where dowel pins are desired are then marked with ink, and dowel pins inserted in the corresponding blind holes.

All of the prior art methods for locating dowel pins in a cast dental arch, including those disclosed in Zeiser and Kiefer, require the determination of dowel pin locations to be made with impressions fixed and stabilized in position relative to reference points on a specially designed impression mounting or carrier plate. Prior art systems also require that a fixed relationship exist between the base plate and mounting plate. This requirement demands elaborate procedures for stabilizing, "boxing," i.e., providing an enclosure for holding liquid die stone and supporting a base plate in an established relationship to the impression. Also, all undercut areas of the negative dental impression, which has a irregular shape that varies in size from one patient to another, must be "blocked out" or trimmed away from the impression. This is to prevent liquid die stone from being trapped in irregular regions of the impression, which would hinder removal of a cast dental arch from the impression.

The present invention was conceived of to provide an improved method and apparatus for producing dental models that overcome certain limitations of prior art systems.

OBJECTS OF THE INVENTION

An object of the present invention is to provide an improved method and apparatus for producing dental models which utilizes materials and/or apparatus which are inherently lower in cost than prior methods and apparatus.

Another object of the invention is to provide a method and apparatus for making dental models which eliminates the requirement for a relatively heavy carrier plate, thus reducing mass to be vibrated during solidification of die stone in a dental impression.

Another object of the invention is to provide a method and apparatus for making dental models which affords greater ease of use than prior art methods.

Various other objects and advantages of the present invention, and its most novel features, will become apparent to those skilled in the art by perusing the accompanying specifications, drawings and claims.

It is to be understood that although the invention disclosed herein is fully capable of achieving the objects and providing the advantages described, the characteristics of the invention described herein are merely illustrative of the preferred embodiment. Accordingly, we do not intend that the scope of our exclusive rights and privileges in the invention be limited to details of the embodiments described. We do intend that equivalents, adaptations and modifications of the invention reasonably inferable from the description contained herein be included within the scope of the invention as defined by the appended claims.

SUMMARY OF THE INVENTION

Briefly stated, the present invention comprehends an improved method and apparatus for producing dental models of the type used in the fabrication of dentures, partial dentures, crowns, jackets, bridges and implant supported restorations, all of which may employ metals, plastics and/or ceramic materials. The improved method and apparatus according to the present invention employs a pre-fabricated base plate of generally uniform thickness and a polygonal outline. A positioning matrix comprising a flat rigid plate with a polygonal perforation or aperture through its thickness dimension is also part of the present invention. The perimetric walls surrounding the aperture are adapted to fit tightly around the perimeter of the base plate, which is removably insertable into the positioning matrix.

The dental modeling method according to the present invention includes placing the upper, trimmed peripheral border of a negative dental impression in contact with the lower flat side of the positioning matrix plate, and forming a liquid-tight seal between the upper perimeter of the impression and lower surface of the plate. The seal is simply and conveniently formed by first kneading a small quantity of silicone putty or similar resilient sealing material into a rope-like shape, and then using the rope to form a bead joining the upper peripheral border of the impression to the lower surface of the positioning matrix plate, the bead encircling the perimeter of the aperture through the plate.

A relatively thin transfer plate made of a dimensionally stable material and having a polygonal outline substantially identical in size and shape to that of the base plate and to that of the aperture through the positioning matrix plate is then inserted into the aperture, in overlying contact with the upper surface of the dental impression. A marking pen or pencil is then used to mark on the upper surface of the transparent transfer plate those locations where it is desired to provide dowel pins in the base plate for supporting removable sections, or dies in a cast dental model or arch. The marked transfer plate is then removed from the positioning matrix plate, and placed in overlying conformal contact with a base plate. A clamp which conforms to the perimeters of the base plate and transfer plate is then placed around the two plates and tightened. Holes are then drilled into the upper surface of the base plate opposite the transfer plate, at each of the locations indicated by the marks on the transfer plate. A drill press of the type having a drill which projects upwards through a work table at a location indicated by an index pointer which projects downwards from a position above the table provides a convenient means for drilling the required holes.

The drilled base plate is then removed from the clamp, and dowel pins inserted into the holes. Next, liquid die stone is poured into the dental impression through the aperture of the positioning matrix plate attached to upper surface of the impression. The base plate is then inserted into the aperture, upper or pin side down, the pins protruding into the liquid die stone, which is then allowed to harden. After the die stone has hardened, the base plate, cast dental arch, and dental impression are pushed en masse down through the aperture in positioning matrix plate. The bead of sealing material is removed from the bottom surface of the positioning matrix plate, either before or after the previously described step, as desired. Next, the negative dental impression forming the mold for the cast dental arch is separated from the dental arch. The arch is then separated from the base plate to permit sawing the cast arch into individual segments or dies. Each of the dies has two downwardly protruding dowel pins cast into the die, permitting each die to be returned to a precise location on the base plate, by inserting the dowel pins into the appropriate holes in the upper surface of the base plate.

In a variation of the novel method and apparatus according to the present invention, the transparent transfer plate and holding clamp are not used. Instead, a transparent base plate is inserted into the aperture of the positioning matrix plate, marked, and drilled.

DESCRIPTION OF THE PREFERRED EMBODIMENTS

Referring now to FIGS. 1 through 16, methods and apparatus for dental modeling using a polygonally apertured positioning matrix plate according to the present invention are depicted.

Figure 1:
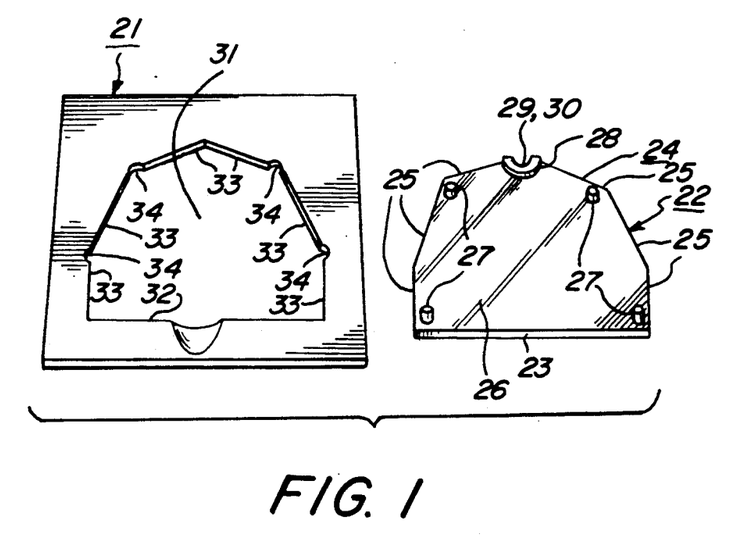
FIG. 1 is an upper plan view of a novel positioning matrix plate and base plate forming part of the present invention.

As shown in FIG. 1, one embodiment of the apparatus 20 according to the present invention includes a positioning matrix plate 21 and a base plate 22. Base plate 22 is of generally uniform thickness and is fabricated from a dimensionally stable, transparent material such as acrylic or polycarbonate plastic. Base plate 22 has a generally semicircular shaped outline with a straight chordal base wall 23 and a generally semicircular or arch-shaped wall 24. Semicircular wall 24 is preferably modified from a curvilinear shape to the shape of a polygon circumscribed around the curvilinear arch. Thus, as shown in FIG. 1, "semicircular" wall 24 has six generally straight polygonal wall surfaces 25, instead of smooth curvilinear wall surfaces. As will become apparent in the ensuing descriptions, the exact number, size and intersection angles of polygonal wall 25 may be varied as desired. However, the polygonal outline of base plate 22 should not be rotationally symmetric, for reasons which will become apparent from the ensuing description of the invention.

The size and shape of base plate 22 are adapted to conformally fit over the concave upper surface of a standard full-jaw negative dental impression. Thus, base plate 22 would typically have a base wall length of approximately 2¾ inches, while semiconductor wall 24 would have a radius of about 1⅜ inches. Base plate 22 may have any convenient thickness, typically ¼ inch. As shown in FIG. 1, the flat lower wall surface 26 of base plate 22 has a plurality of short, upwardly protruding bosses. At least three bosses are provided; one boss 27 at each of the two base corners of base plate 22, and one boss 28 at the peak of semicircular wall 24. Corner bosses 27 have a generally cylindrical shape. Peak boss 28 has a generally crescent shape and forms a concave notch 29 in the peak 30 of semicircular wall 24. The purpose of bosses 27 and 28 will be explained below.

As shown in FIG. 1, the apparatus 10 according to the present invention includes a "positioning matrix plate" 21. Positioning matrix plate 21 is a thin, uniform thickness plate fabricated from a dimensionally stable material. A wide variety of materials are thus suitable for the manufacture of positioning matrix plate 21. Examples of such materials include thermosetting plastics, thermoplastics such as acrylic, or composites such as fiberglass reinforced epoxy sheets of the kind used to manufacture printed circuit boards. The outline shape of positioning matrix plate may be any convenient shape, such as the rectangular shape shown in FIG. 1.

Preferably, a concave thumbnail-shaped depression 21B is formed in the upper surface 21A of matrix plate 21, the wider "cuticle" of the depression penetrating base wall 32.

As shown in FIG. 1, an aperture 31 is provided through the thickness dimension of positioning matrix plate 21. Aperture 31 is of the proper size and shape to insertably receive, in a relatively tight interference fit, base plate 21. Thus, as shown in FIG. 1, aperture 31 has a straight base wall 32 and a plurality of intersecting polygonal walls 33 forming a symmetrical, arch-like shape. Also, each intersection vertex of adjacent polygonal walls 33 is preferably notched slightly, thereby forming a plurality of semicircular relief holes 34 adjacent to at least some of the vertices of polygonally shaped base plate 22, when the base plate is inserted into aperture 31 of positioning matrix plate 21. The method of using the apparatus of FIG. 1 will now be described.

Figure 2:
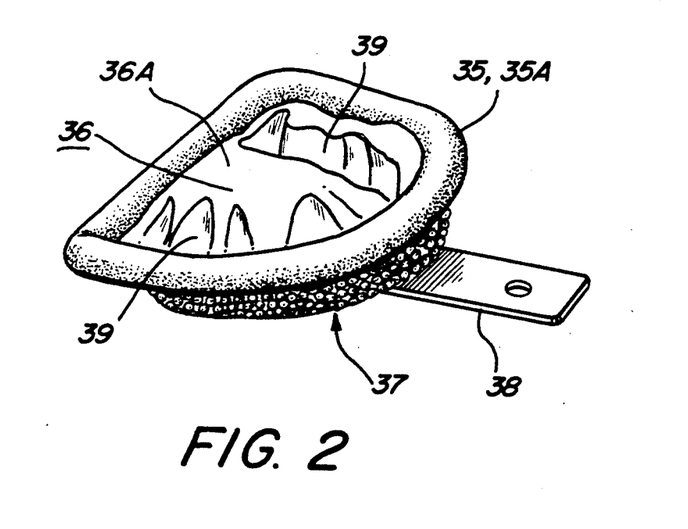
FIG. 2 is an upper perspective view of a negative dental impression provided with a bead of material as part of the method according to the present invention.
Figure 3:
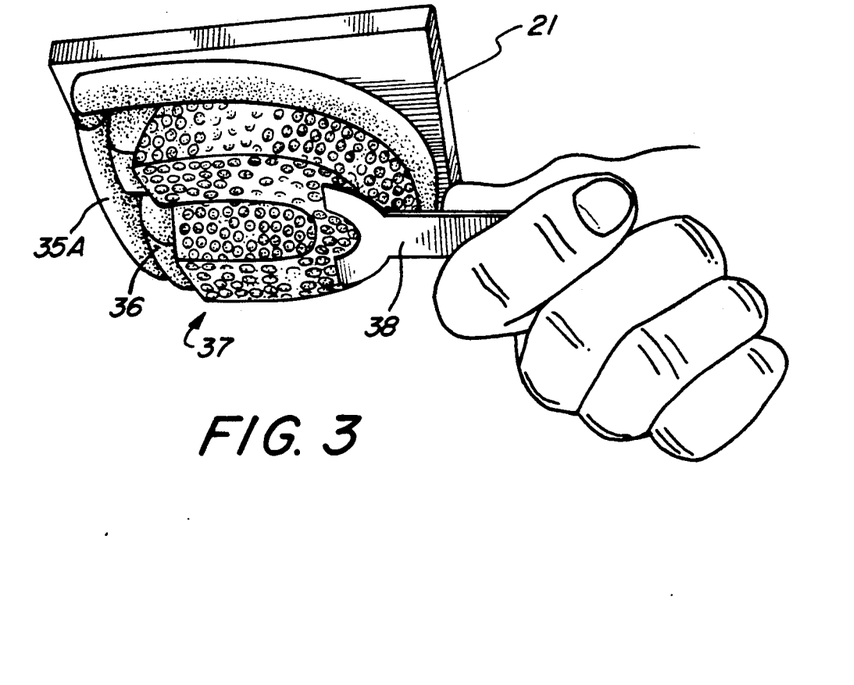
FIG. 3 is a lower perspective view showing the positioning matrix plate of FIG. 1 attached to the bead and impression of FIG. 2.

As shown in FIG. 2, the first step in practicing the method of the present invention is the attachment of rope-shaped length 35 of silicone putty or similar resilient putty-like sealing material formed into a bead 35A around the upper peripheral border of negative dental impression 36 contained in holder 37 having a handle 38 protruding outwards from the base of the holder. Next, positioning matrix plate 21 is pushed down into sealing contact with bead 35A, as shown in FIG. 3. As shown in FIG. 3, bead 35A is adjacent to and surrounds the lower opening of aperture 31.

Figure 4:
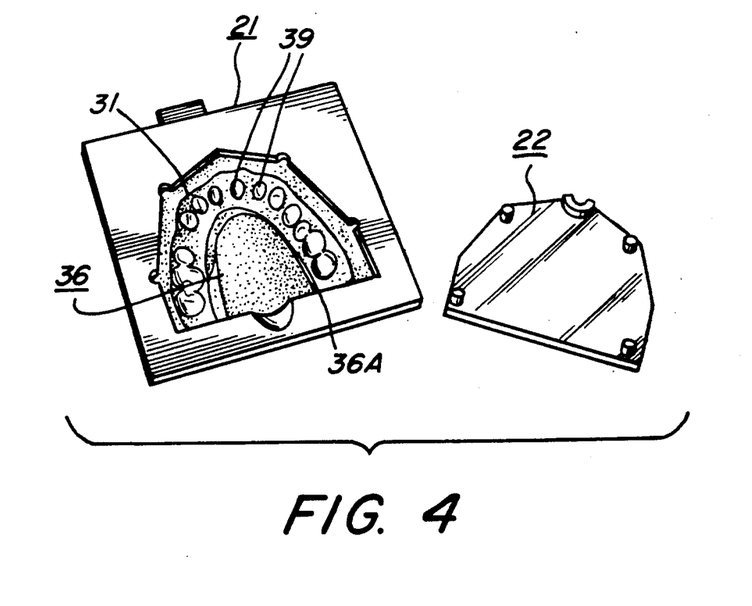
FIG. 4 is an upper perspective view of the assembly of FIG. 3, prior to the insertion of a base plate into the matrix positioning plate.
Figure 5:
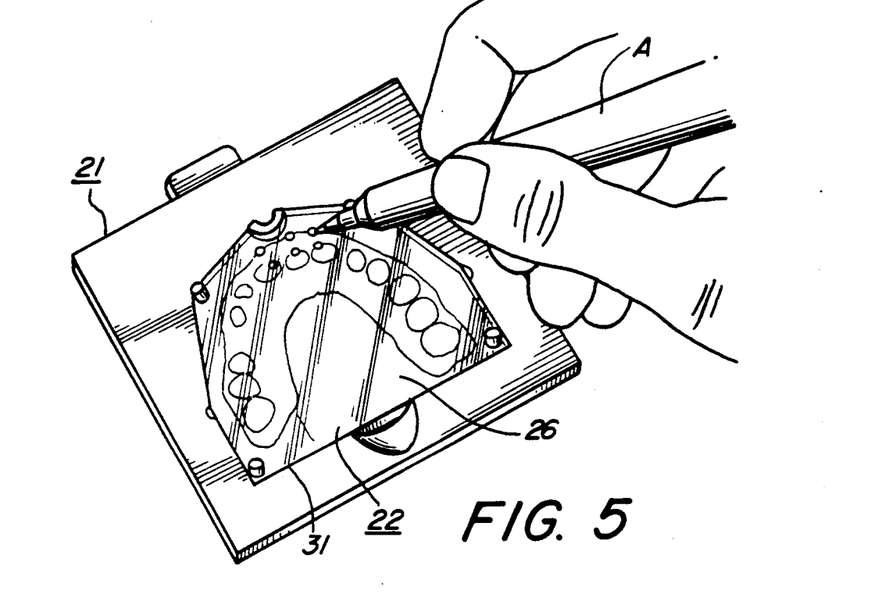
FIG. 5 is an upper perspective view of the base plate of FIG. 1 inserted into the aperture of the matrix positioning plate of FIG. 4, and showing the method of marking desired locations for dowel pins on the base plate.

With dental impression 36 secured to matrix positioning plate 21 by bead 35A of silicone rubber, as described above, a transparent base plate 22 is inserted into aperture 31 of the matrix plate, as shown in FIGS. 4 and 5. Base plate 22 is pushed down into aperture 31 of positioning matrix plate 21 sufficiently far for the upper surface 22A of the base plate to contact the upper surface 36A of dental impression 36. Then, as shown in FIG. 5, a fine pointed felt tip pen A or any other suitable marking means is used to mark on the lower surface 26 of base plate 22 the desired location of each pair of dowel pins for each tooth die, by viewing the impression 39 of each such tooth through the transparent base plate and marking dots on the plate directly above the impression.

After a base plate 22 has been marked to indicate the desired location of all dowel pins on the base plate, the base plate is removed from matrix plate 21. Inserting a finger tip into depression 21B in the upper surface 21A of the matrix plate facilitates removal of base plate 22. Holes of the proper size to receive dowel pins are then formed in the base plate. A convenient method of forming the dowel pin holes is shown in FIG. 6.

Figure 6:
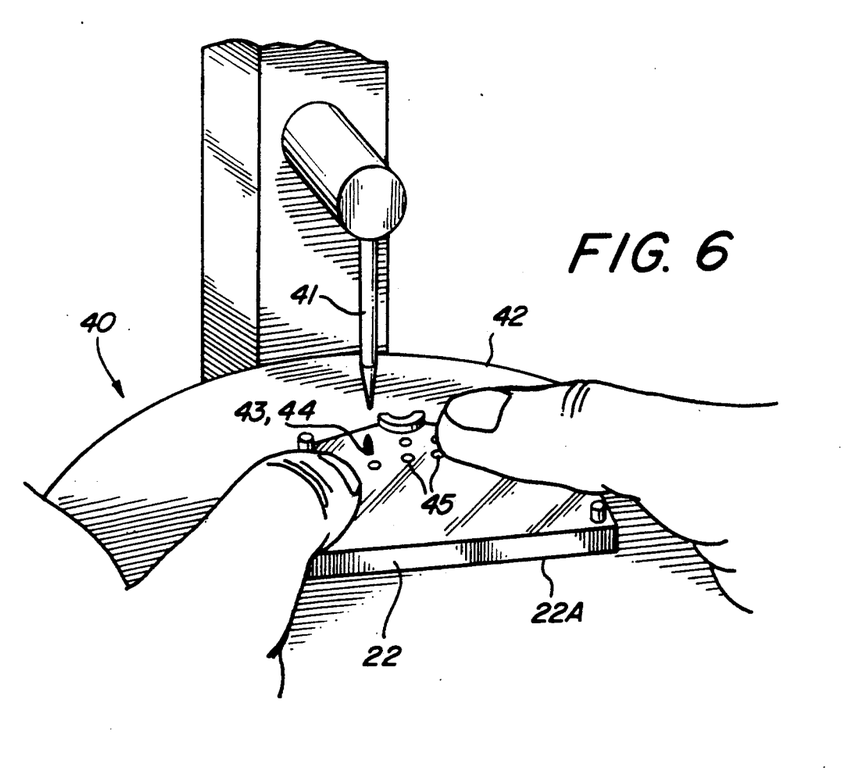
FIG. 6 is an upper perspective view of the marked base plate of FIG. 5 being drilled.

As shown in FIG. 6, a drill press 40 of the type having an index pointer 41 positioned above a work table 42 and precisely aligned with the point of a drill bit 43 which is extendable upwards through an aperture 44 in the table may conveniently be used to drill dowel pin holes 45 in upper surface 22A of base plate 22. The use of index pointer 41 is not necessary when drilling a transparent base plate, but provides a convenient means for forming holes in non-transparent base plates used in another embodiment of the invention described below.

Figure 7:
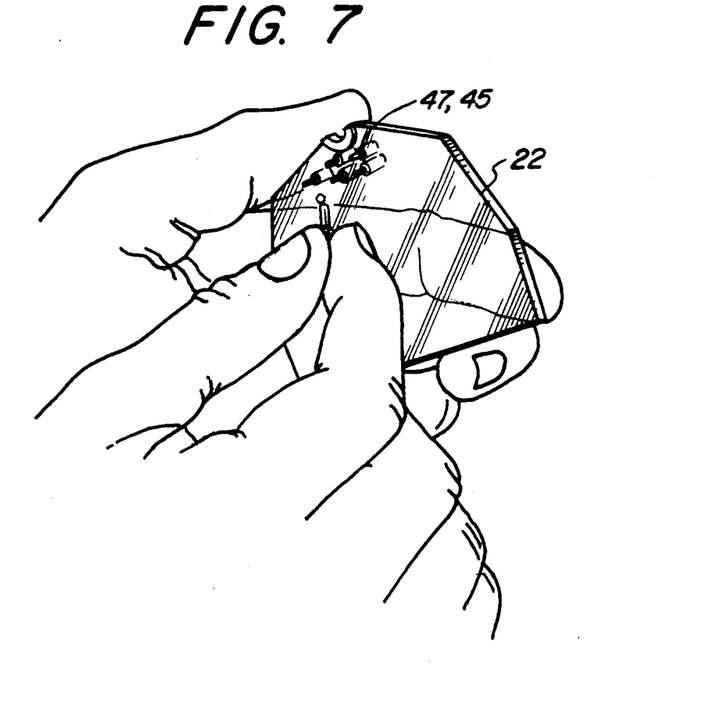
FIG. 7 is a perspective view of dowel pins being inserted into the holes drilled into the base plate as shown in FIG. 6.

After holes 45 have been drilled into the upper surface 22A of base plate 22 at each desired dowel pin location, a dowel pin 47 is inserted into each hole 45, as shown in FIG. 7.

Figure 8:
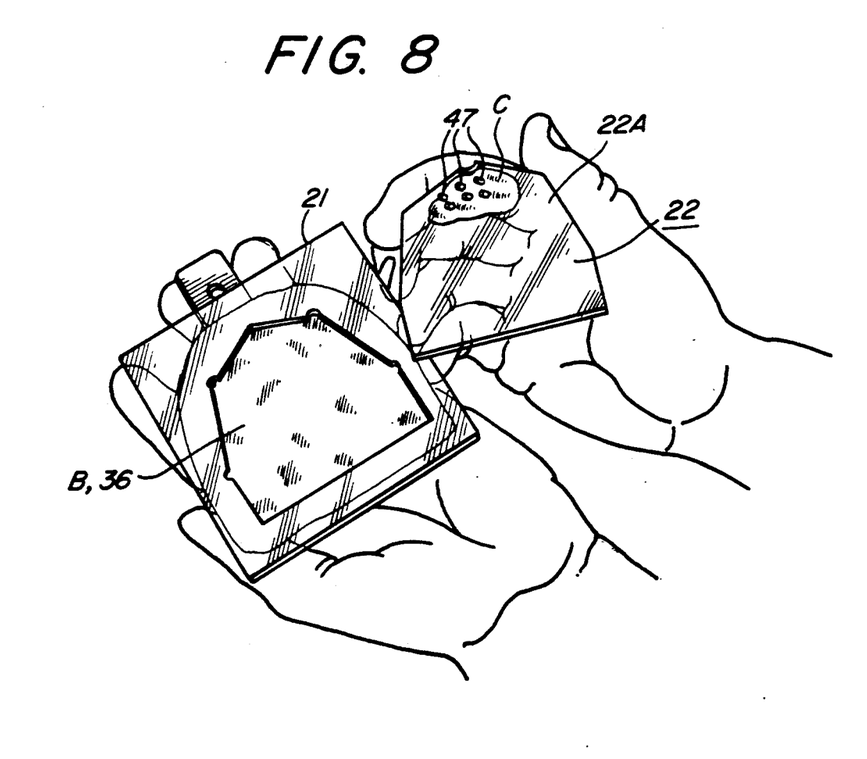
FIG. 8 is an upper perspective view showing a negative dental impression attached to the matrix positioning plate of FIG. 1, showing the impression filled with liquid die stone, and showing a base plate of the type shown in FIG. 1 provided with dowel pins, preparatory to inserting the base plate into the aperture of the positioning matrix plate.

Referring now to FIG. 8, after dowel pins 47 have been inserted into holes 45 in base plate 22, liquid die stone B is poured through aperture 31 of positioning matrix plate 21 into dental impression 36 attached to the lower surface of the positioning matrix plate. Small amounts C of semi-liquid die stone may be adhered to portions of the upper surface 22A of base plate 22, adjacent dowel pins 47, if desired.

Figure 9:
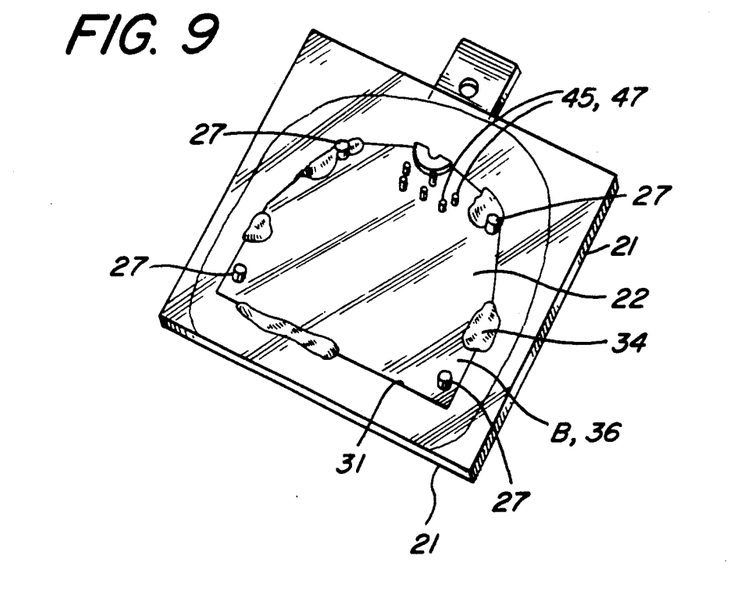
FIG. 9 is an upper perspective view of the matrix positioning plate and base plate of FIG. 8 during the setting or curing of liquid die stone.

Referring now to FIG. 9, a base plate 22 with inserted dowel pins 47, prepared as described above and depicted in FIG. 8, is inserted into aperture 31 of matrix positioning plate 21 attached to a dental impression 36 holding liquid die stone B. As shown in FIG. 9, relief holes 34 at the intersections of walls of the aperture 31 in positioning matrix plate 21 allow globules D of liquid die stone B to be displaced upwards through the relief holes as the base plate 22 is pushed downwards through the aperture until it seats against the upper surface 36A of dental impression 36. In this position, dowel pins 47 are submerged in liquid die stone B, and become embedded therein when the die stone hardens.

Figure 10:
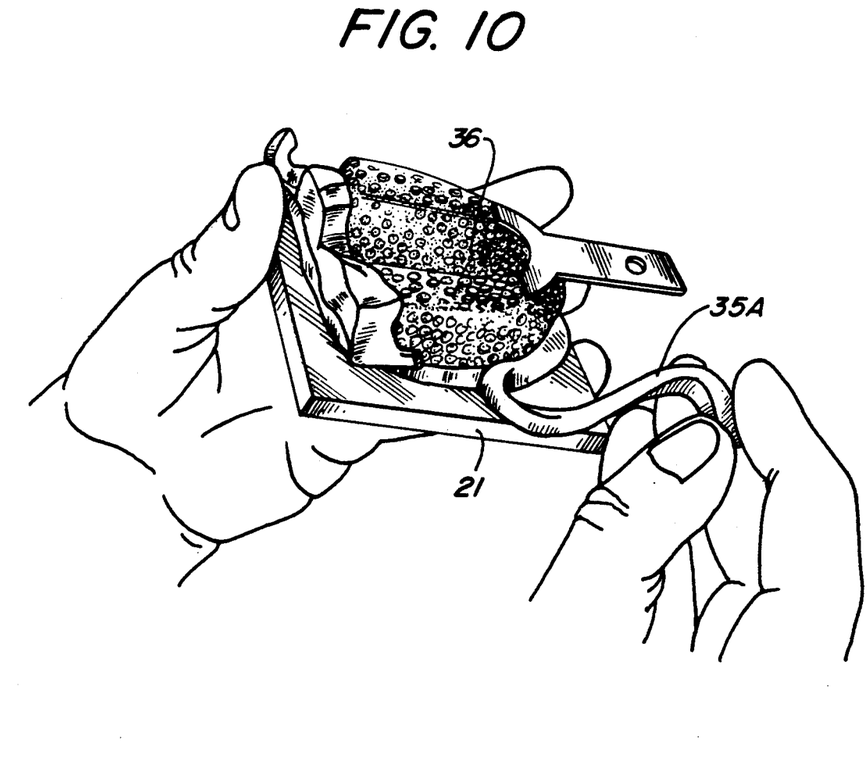
FIG. 10 is a lower perspective view of the sealing bead being removed from the matrix positioning plate of FIG. 9.

Referring now to FIG. 10, after die stone B has hardened, bead 35A of silicone putty is removed from the lower surface of matrix positioning plate 21. Base plate 22, dental impression 36, and cast dental arch 48 are then pushed downwards en masse through aperture 31 in matrix positioning plate 21, as shown in FIG. 11.

Figure 11:
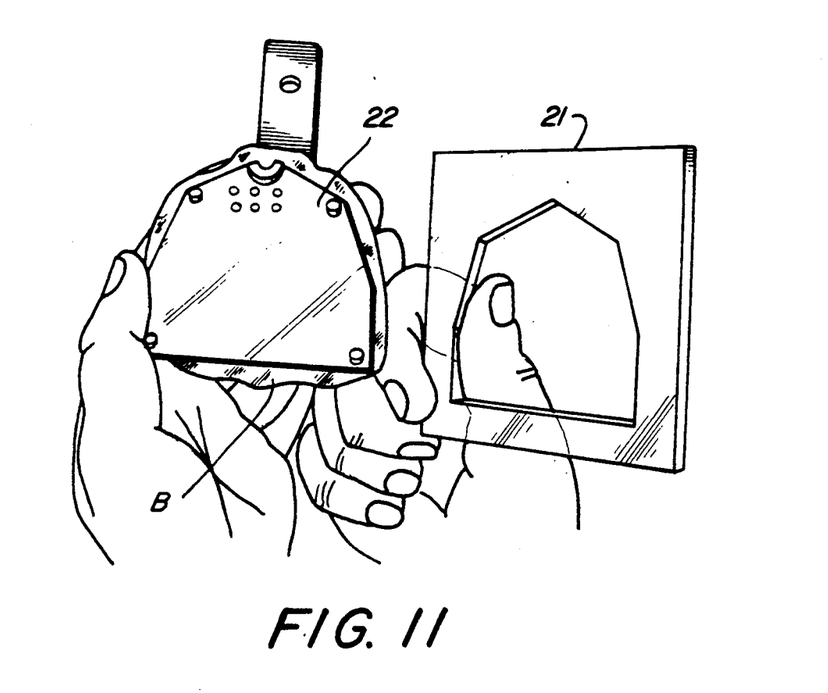
FIG. 11 is an upper perspective view of the cast dental arch having been removed from the matrix positioning plate of FIG. 10.
Figure 12:
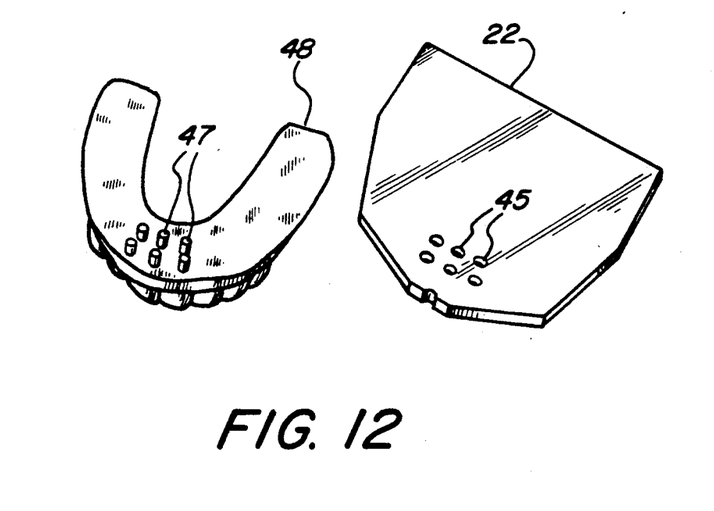
FIG. 12 is a perspective view of the cast dental arch of FIG. 11 removed from the negative impression mold, and separated from the base plate.
Figure 13:
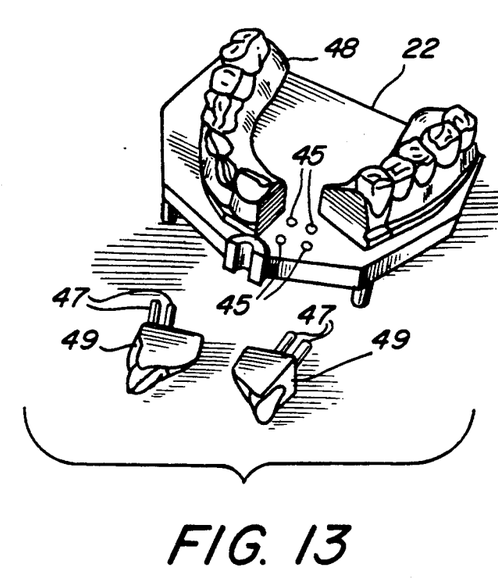
FIG. 13 is an upper perspective view of the cast dental arch of FIG. 12 re-attached to the base plate, with certain segments or dies of the arch removed from the base plate.

Referring now to FIGS. 11 and 12, dental impression 36 is then pried away from cast dental arch 48 and base plate 22. Dental arch 48 may then be easily separated from base plate 22 by tapping or other means, dowel pins 47 being of the proper size and shape to fit snugly, but not too tightly, into holes 45 in the base plate. Then, as shown in FIG. 13, dental arch 48 may be segmented by means of saw cuts into individual dies 49. Dies 49 may then be used to fabricate restorations for individual teeth, and returned to precisely repeatable locations in base plate 22 to check the shape and fit of each of the restorations during the fabrication of the restorations.

Figure 14:
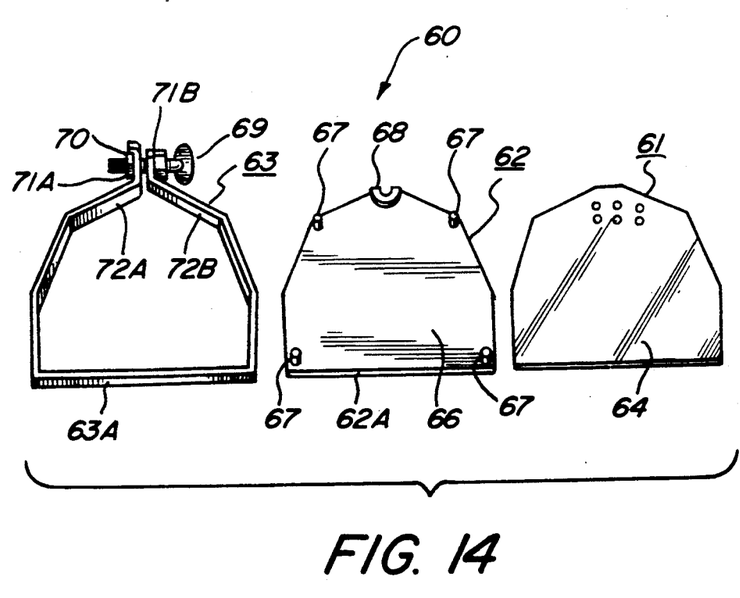
FIG. 14 is an upper perspective view of a base plate, transfer plate, and clamp used in an alternate embodiment of the present invention.
Figure 15:
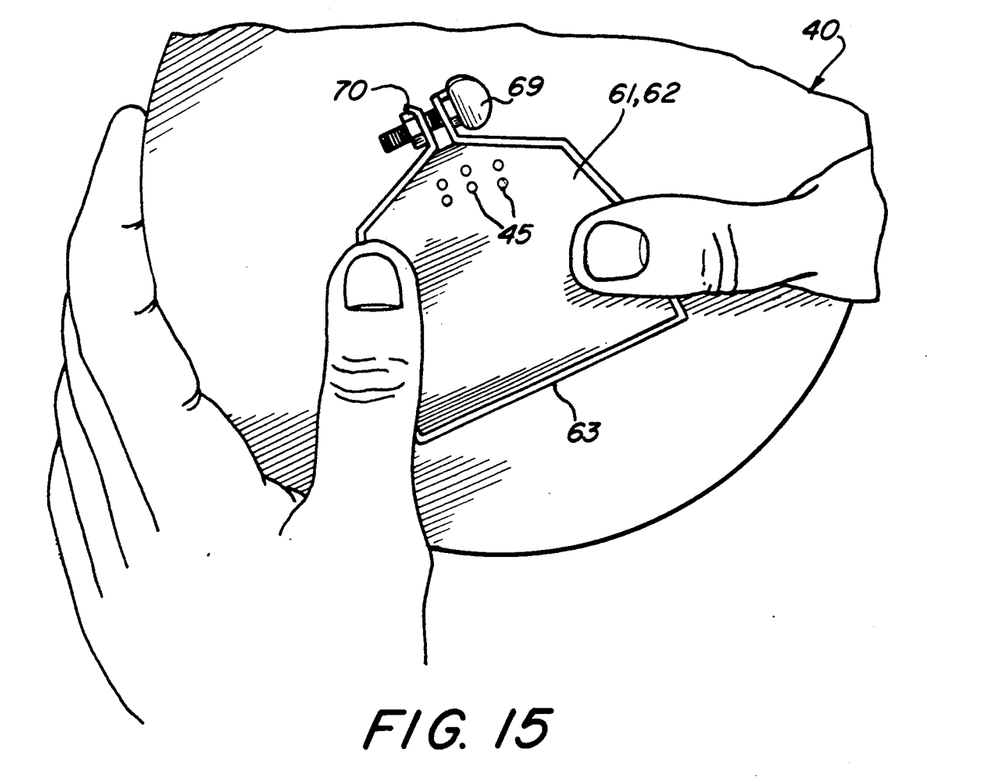
FIG. 15 is an upper perspective view of the transfer plate and base plate of FIG. 14 having been clamped together and being drilled at locations previously marked on the transfer plate in a manner similar to that shown in FIG. 5.

FIGS. 14 and 15 illustrate an alternate embodiment of the novel dental modeling method and apparatus according to the present invention.

In embodiment 60 shown in FIGS. 14 and 15, a base plate 62 substantially identical in size and shape to base plate 22 is used. Base plate 62 is also made of a dimensionally stable material, but need not be transparent.

Embodiment 60 of the apparatus according to the present invention also uses a transfer pate 61. Transfer plate 61 is made of a dimensionally stable material and has a polygonal outline shape substantially identical to that of base plate 62. However, transfer plate 61 is required to be transparent. Also, transfer plate is preferably thinner than base plate 62, having a thickness of approximately $\frac{1}{8}$ inch or less, for example.

Embodiment 60 of the present invention also includes a clamp 63, the structure and function of which are described below.

The method of using the novel embodiment 60 of the dental modeling apparatus according to the present invention has a substantial number of steps in common with those previously described for the basic embodiment 20 of the novel apparatus. Thus, embodiment 60 includes a positioning matrix plate 21, utilized in precisely the same way as depicted in FIGS. 2 through 5 and described above. However, in embodiment 60, transfer plate 61 rather than base plate 22 is inserted into aperture 31 of positioning matrix plate 21, for the step shown in FIG. 5. Here, upper surface 64 of transfer plate 61 is marked with a pen A at those points where it is desired to locate dowel pins. Since transfer plate 61 may be thinner than base plate 22 or base plate 62, upper surface 64 of the transfer plate may be closer to dental impression 36 than upper surface 46 of base plate 22, were the base plate to be used. Closer spacing between the surface to be marked and the dental impression reduces parallax errors, allowing the locations of dowel pin hole drill points to be determined more precisely relative to the underlying dental impression.

After the location of each desired dowel pin hole has been marked on the upper surface of transfer plate 61, as shown in FIG. 5, the marked transfer plate is removed from aperture 31 of positioning matrix plate 21. Then, as shown in FIG. 14 and 15, transfer plate 61 is placed down on top of bosses 67 and 68 protruding away from the lower wall surface 66 of base plate 62. Transfer plate 61 and base plate 62 are held in a longitudinally aligned, contacting relationship to one another by any convenient means, such as clamp 63. Clamp 63 comprises a flat metal strip 63A formed into a polygon which conforms to the polygonal wall of base plate 62 and transfer plate 61. The clamp 63 is tightened around the polygonal perimeter of base plate 62 and transfer plate 61 by means of bolt 69 and nut 70. Bolt 69 passes through aligned holes 71A and 71B through opposite lateral ends 72A and 72B, respectively, of strip 63A.

With base plate 62 and transfer plate 61 held together by means of clamp 63, as described above, dowel pin holes 45 are formed in the upper surface 62A of base plate 62 at the locations marked on the upper surface 64 of transfer plate. Thus, as shown in FIG. 15, the same type of drill press 40 used to form holes 45 in base plate 22 may be used to form holes 45 in base plate 62. Bosses 67 and 68, which protrude outwards from the lower wall surface 66 of base plate 62, hold the transfer plate 61 spaced above the base plate during the drilling operation, thus preventing holes from being formed in the transfer plate and thereby permitting re-use of the transfer plate.

Figure 16:
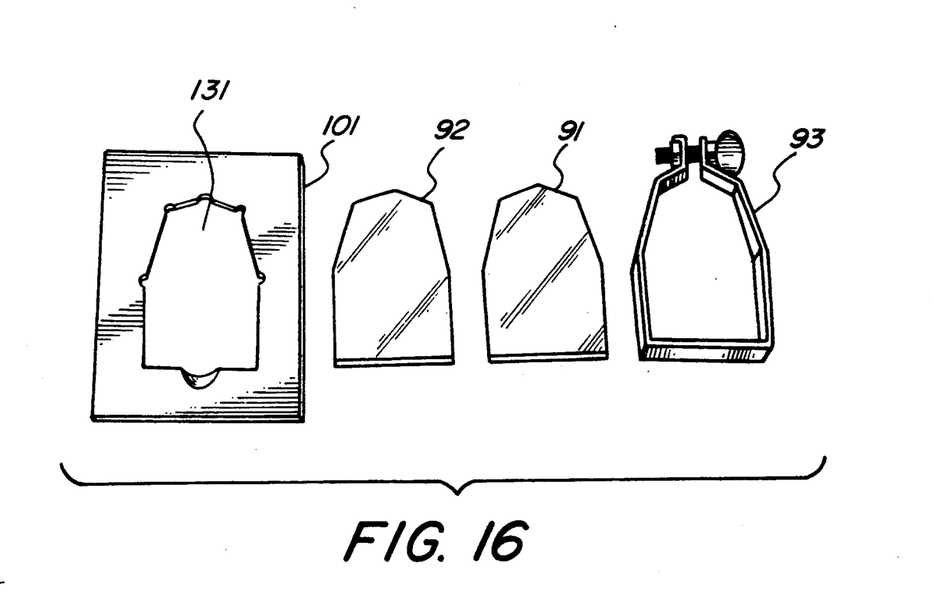
FIG. 16 is an upper perspective view of components of another version of the apparatus according to the present invention which is particularly useful in the fabrication of quadrant or partial dental models.

FIG. 16 illustrates a variation of the embodiment 60 of the apparatus shown in FIGS. 14 and 15. In the variation 90 shown in FIG. 16, base plate 92, transfer plate 91 and clamp 93 are shaped like half sections of corresponding elements 62, 61 and 63, respectively. Thus, variation 90 is suitable for making dental models of partial upper or lower jaw sections, sometimes referred to as quadrants, using a matrix plate 101 having a polygonal aperture 131 matching the perimetric outline of base plate 92 and transfer plate 91. If base plate 92 is made of a transparent material, transfer plate 91 and clamp 93 may be dispensed with, and the method depicted in FIGS. 1 through 5 used to mark the base plate.

What is claimed is:

1. An apparatus for fabricating a dental model which is a positive replica of teeth and connected soft tissue from a negative impression mold previously made from said teeth and soft tissue, said apparatus comprising:
    a. a positioning matrix, said positioning matrix comprising a thin matrix plate of generally uniform thickness fabricated from a dimensionally stable material, said matrix plate having a polygonal aperture through its thickness dimension, said aperture having a closed perimeter wall located entirely within said matrix plate, and
    b. a base plate of generally uniform thickness fabricated from a dimensionally stable, transparent material, said base plate having a perimetric outline substantially identical in shape to the perimetric outline of said aperture in said matrix plate, whereby said base plate may be removably inserted in a direction perpendicular to the plane of said matrix plate, and reinserted in a precisely repeatable location, into said aperture of said matrix plate, and whereby a dental impression may be attached to a lower surface of said matrix plate, said base plate inserted into said aperture of said matrix plate in overlying relationship to said impression, and marks made at those locations on said base plate where dowel pins are desired, said locations being determined in relationship to said impression by viewing said impression through said transparent base plate.

2. The apparatus of claim 1 wherein said polygonal aperture is further defined as having the approximate shape of a semicircle, having a flat chordal wall, the arcuate portion of said semicircle being approximated by a plurality of circumscribed, straight polygonal walls.

3. The apparatus of claim 1 wherein at least one intersection of adjacent walls of said aperture of said matrix plate has a notch extending through the thickness dimension of said base plate, thereby providing a relief passageway for air and liquid die stone when said base plate is inserted into said aperture of said matrix plate.

4. The apparatus of claim 1 wherein said base plate is further defined as having a plurality of equal height bosses protruding away from the lower surface of said base plate, thereby holding the base plate a spaced distance above a horizontal surface on which the base plate is placed.

5. An apparatus for fabricating a dental model which is a positive replica of teeth and connected soft tissue from a negative impression mold previously made from said teeth and soft tissue, said apparatus comprising;
    a. a positioning matrix plate, said positioning matrix plate comprising a thin plate of generally uniform thickness, fabricated from a dimensionally stable material, said matrix plate having a polygonal aperture through its thickness dimension,
    b. a base plate of generally uniform thickness fabricated from a dimensionally stable material, said base plate having a perimetric outline substantially identical in shape to the perimetric outline of said aperture in said matrix plate, whereby said base plate may be removably inserted, and reinserted in precisely repeatable location into said aperture,
    c. a transfer plate of thin generally uniform thickness, said transfer plate being fabricated from a transparent, dimensionally stable material and having a perimetric outline substantially identical in shape to the perimetric outline of said aperture in said matrix plate, whereby said transfer plate may be removably inserted, and reinserted in a precisely repeatable location, into said aperture of said matrix plate, and whereby a dental impression may be attached to a lower surface of said matrix plate, said transfer plate inserted into said aperture of said matrix plate in overlying relationship to said impression, and marks made at those locations on the surface of said transfer plate where dowel pins are desired in said base plate, and
    d. clamping means for holding said transfer plate in a longitudinally aligned, overlying relationship over the lower surface of said base plate, whereby holes for dowel pins may be made in those locations in the upper surface of said base plate which are longitudinally aligned with said marks on said transfer plate.

6. The apparatus of claim 5 wherein said polygonal aperture is further defined as having the approximate shape of a semicircle, having a flat chordal wall, the arcuate portion of said semicircle being approximated by a plurality of circumscribed, straight polygonal walls.

7. The apparatus of claim 5 wherein at least one intersection of adjacent walls of said aperture of said matrix plate has a notch extending through the thickness dimension of said base plate, thereby providing a relief passageway for air and liquid die stone when said base plate is inserted into said aperture of said matrix plate.

8. The apparatus of claim 5 wherein said base plate is further defined as having a plurality of equal height bosses protruding away from the lower surface of said base plate, thereby holding said transfer plate a spaced distance above said base plate when said holes are formed in said base plate.

9. The apparatus of claim 5 wherein said clamping means comprises a strap conformable around the outer perimetric wall surfaces of said base plate and said transfer plate, and means for tightening said strap around said perimetric walls.

* * * * *

REEXAMINATION CERTIFICATE (2345th)
United States Patent [19]
Honstein et al.

[11] B1 5,098,290
[45] Certificate Issued Jul. 26, 1994

[54] DENTAL MODELING METHOD AND APPARATUS USING APERTURED MATRIX PLATE

[75] Inventors: Jerry P. Honstein, 6543 E. Circulo Dali, Anaheim Hills, Calif. 92807; Anthony B. Siragusa, Anaheim Hills, Calif.; Richard Barnes, Mission Viejo, Calif.; Victor M. Barajas, San Gabriel, Calif.

[73] Assignee: Jerry P. Honstein, Anaheim Hills, Calif.

Reexamination Request:
No. 90/002,898, Nov. 27, 1992

Reexamination Certificate for:
Patent No.: 5,098,290
Issued: Mar. 24, 1992
Appl. No.: 579,300
Filed: Sep. 7, 1990

[51] Int. Cl.$^5$ .................................. A61C 19/00
[52] U.S. Cl. ........................ 433/74; 433/49; 433/50
[58] Field of Search ............ 433/74, 49, 50, 53, 433/72, 213; 264/16, 17

[56] References Cited

U.S. PATENT DOCUMENTS 4,371,339  2/1983  Zeiser ............................. 433/53
4,708,835  11/1987  Keifer ............................ 433/74

FOREIGN PATENT DOCUMENTS 0030312  1/1984  European Pat. Off. .

OTHER PUBLICATIONS

"Girrbach Dental" catalog, 1986/1987.
"Girrbach Dental" information sheet, 1988/1989.

Primary Examiner—Cary E. O'Connor
Attorney, Agent, or Firm—William L. Chapin

[57] ABSTRACT

An improved method and apparatus for making cast dental models having integral dowel pins permitting segments or dies of a model to be attached and reattached to a base plate in a precise location, by means of holes in the base plate adapted to insertably receive the dowel pins, is disclosed. The apparatus includes a base plate having a generally semi-circular shape, the arcuate outer wall surface of which is modified to have flat walls approximating the shape of a circumscribed polygon. A matrix positioning plate has a polygonal aperture through its thickness dimension adapted to insertably receive the base plate. A negative dental impression is attached to a first, lower surface of the matrix plate, and a transparent transfer plate of the same size and shape as the base plate inserted into the aperture of the matrix plate. Marks are placed at those locations of the transfer plate where dowel pins are desired to engage parts of the dental impression viewed through the transfer plate. The marked transfer plate is then clamped in overlying conformal relationship to a base plate, and holes formed in the base plate at the locations indicated by the marks. In another embodiment of the invention which dispenses with the requirement for a transfer plate, a transparent base plate is inserted into the matrix plate, marked and removed. Holes are then formed in the base plate at the marked locations.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 3 is cancelled.

Claims 1, 5 and 7 are determined to be patentable as amended.

Claims 2, 4, 6, 8 and 9, dependent on an amended claim, are determined to be patentable.

1. An apparatus for fabricating a dental model which is a positive replica of teeth and connected soft tissue from a negative impression mold previously made from said teeth and soft tissue, said apparatus comprising:
   a. a positioning matrix, said positioning matrix comprising a thin matrix plate of generally uniform thickness fabricated from a dimensionally stable material, said matrix plate having a polygonal aperture through its thickness dimension, said aperture having a closed perimeter wall located entirely within said matrix plate, *at least one intersection of adjacent walls of said aperture of said matrix plate having a notch extending through the thickness dimension of said matrix plate, thereby providing a relief passageway for air and liquid die stone when a base plate is inserted into said aperture of said matrix plate*, and
   b. a base plate of generally uniform thickness fabricated from a dimensionally stable, transparent material, said base plate having a perimetric outline substantially identical in shape to the perimetric outline of said aperture in said matrix plate, whereby said base plate may be removably inserted *in a direction perpendicular to the plane of said matrix plate*, and reinserted in a precisely repeatable location, into said aperture of said matrix plate, and whereby a dental impression may be attached to a lower surface of said matrix plate, said base plate inserted into said aperture of said matrix plate in overlying relationship to said impression, and marks made at those locations on said base plate where dowel pins are desired, said locations being determined in relationship to said impression by viewing said impression through said transparent base plate.

5. An apparatus for fabricating a dental model which is a positive replica of teeth and connected soft tissue from a negative impression mold previously made from said teeth and soft tissue, said apparatus comprising:
   a. a positioning matrix plate, said positioning matrix plate comprising a thin plate of generally uniform thickness, fabricated from a dimensionally stable material, said matrix plate having a polygonal aperture through its thickness dimension,
   b. a base plate of generally uniform thickness fabricated from a dimensionally stable material, said base plate having a [perimetric outline] *perimeter* substantially identical in shape to the [perimetric outline] *perimeter* of said aperture in said matrix plate, whereby said base plate may be removably inserted, and reinserted in a precisely repeatable location into said aperture,
   c. a transfer plate of this generally uniform thickness, said transfer plate being fabricated from a transparent, dimensionally stable material and having a [perimetric outline] *perimeter* substantially identical in shape to the [perimetric outline] *perimeter* of said aperture in said matrix plate, whereby said transfer plate may be removably inserted, and reinserted in a precisely repeatable location, into said aperture of said matrix plate, and whereby a dental impression may be attached to a lower surface of said matrix plate, said transfer plate inserted into said aperture of said matrix plate in overlying relationship to said impression, and marks made at those locations on the surface of said transfer plate where dowel pins are desired in said base plate, and
   d. clamping means for holding said transfer plate in a longitudinally aligned, overlying relationship over the lower surface of said base plate, whereby holes for dowel pins may be made in those locations in the upper surface of said base plate which are longitudinally aligned with said marks on said transfer plate.

7. The apparatus of claim 5 wherein at least one intersection of adjacent walls of said aperture of said matrix plate has a notch extending through the thickness dimension of said [base] *matrix* plate, thereby providing a relief passageway for air and liquid die stone when said base plate is inserted into said aperture of said matrix plate.

* * * * *